United States Patent [19]

Shimkus et al.

[11] Patent Number: 4,926,848
[45] Date of Patent: May 22, 1990

[54] ADJUSTABLE ELASTIC BANDAGE

[76] Inventors: John W. Shimkus, 118 Pulteney St., Hammondsport, N.Y. 14840; Jane M. Brownell, R.D. 4, Box 186, Fort Hill Rd., Bath, N.Y. 14810

[21] Appl. No.: 239,936

[22] Filed: Sep. 2, 1988

[51] Int. Cl.$^5$ .............................................. A61F 13/06
[52] U.S. Cl. .................................... 128/169; 128/166; 128/DIG. 15
[58] Field of Search ................. 128/169, 82, 165, 166, 128/170, 171, DIG. 15; 2/DIG. 6; 24/306; 273/DIG. 30

[56] References Cited

U.S. PATENT DOCUMENTS

| | | | |
|---|---|---|---|
| 1,212,731 | 1/1917 | Banks | 128/169 |
| 1,465,970 | 8/1923 | Cleveland et al. | 128/166 |
| 2,717,437 | 9/1955 | De Mestral | 2/DIG. 6 |
| 3,086,529 | 4/1963 | Munz et al. | 128/DIG. 15 |
| 3,297,026 | 1/1967 | Van Pelt | 128/165 |
| 3,453,696 | 7/1969 | Mates | 24/306 |
| 4,085,746 | 4/1978 | Castiglia | 128/DIG. 15 |
| 4,481,682 | 11/1984 | Hall | 2/DIG. 6 |

Primary Examiner—Stephen R. Crow
Attorney, Agent, or Firm—Howard J. Greenwald

[57] ABSTRACT

An elastic strip, useful as a bandage, is disclosed. The strip contains an adjustable, movable component which contains "VELCRO" (synthetic materials which adhere when pressed together) on both its front and rear faces. The strip also contains a fixed component containing complementary "VELCRO" material on both its front and rear faces.

10 Claims, 1 Drawing Sheet

U.S. Patent — May 22, 1990 — 4,926,848

ADJUSTABLE ELASTIC BANDAGE

FIELD OF THE INVENTION

An adjustable, elastic, wrap-around bandage comprised of two fastener components, at least one of which is adjustable and one of which is fixed, wherein each of the adjustable and fixed fastener components contain complementary fibrous fastener means on at least one of its surfaces.

BACKGROUND OF THE INVENTION

Elastic bandages have been used extensively for many years. Thus, by way of illustration, they have been used to treat strains of muscles and joints, sprains of muscles and joints, local or regional swelling, minor fractures, and simple reduced dislocations. They are also frequently used by people engaged in vigorous physical activity where some external support is desired.

These elastic bandages, often referred to as "Ace bandages," have frequently had their trailing ends secured against accidental displacement when in use by removable clips which removably engage both the trailing end of the bandage and the body thereof. These removable fasteners are frequently referred to as "butterfly clips."

The use of butterfly clips presents several problems. In the first place, unless the elastic bandage with which they are used is wound under considerable tension, it is possible for one or more of the butterfly clips to become disengaged as the patient moves around. In the second place, because elastic bandages are frequently removed and reapplied by patients, the butterfly clips are often misplaced and lost during bandage-changing operations. In the third place, the presence of sharp points on the butterfly clips allows one to accidentally stick himself during application of the bandage or during its use.

The prior art has recognized the problems with using butterfly clips on elastic bandages and has proposed several partial solutions. Thus, U.S. Pat. No. 2,820,456 of Peerless et al. provides an elastic bandage containing an integral attachment buckle having a row of spaced pointed tangs or spurs. U.S. Pat. No. 3,039,461 of Hawie provides an elastic bandage with a permanent fastener made of a deformable material such as sheet metal. U.S. Pat. No. 3,480,012 of Smithers et al. provides a bandage wrap composed of an elongated fabric having exposed crimped fibers on opposite sides thereof and further having patches of minute hook elements designed to engage and grip the crimped fibers and thus secure the bandage. U.S. Pat. No. 3,863,301 of Leveen provides an elastic bandage with a permanent plastic fastener comprised of a set of jaws. However, none of these patents provides an adjustable elastic bandage which can readily and easily be used by a patient.

An adjustable elastic bandage is provided by U.S. Pat. No. 3,005,454 of Bird. The bandage of this patent is provided with upwardly directed teeth 14 which may be brought into engagement with the threads of the bandage to hold the fastener in the desired position. In order to secure this bandage, hooks 18 on one end of the bandage are inserted into holes 16 in adjustable fastener 10.

There are several problems with the adjustable bandage of the Bird patent. In the first place, it is relatively complicated to attach the hooks 18 to the holes 16. In the second place, sharp teeth 14 present no less a danger to the patient than the butterfly clips previously used. In the third place, the use of metallic hooks 18 and teeth 14 does not allow one to readily clean the bandage in a washing machine; the washing of a bandage with sharp metal points together with other clothing presents an obvious danger of damage to the other fabrics. In the fourth place, it does not appear that the fastener 10 of this patent can be utilized regardless of the direction the elastic bandage is wrapped. In the fifth place, the use of metallic components in the Bird device presents the danger that, when one or more of these components are near a joint, motion of the joint will be retarded and discomfort will be caused.

It is an object of this invention to provide an elastic bandage with a permanent, deformable, and adjustable fastener.

It is another object of this invention to provide an elastic bandage which can be washed in a washing machine without presenting the danger of damaging other clothes in the machine or of rusting.

It is another object of this inion to provide an elastic bandage which will present no danger of injury to the patient during application or use.

It is another object of this invention to provide an elastic bandage which can readily and easily be applied to or removed from the body of a patient.

It is yet another object of this invention to provide an elastic bandage possessing a permanently attached fastener which can be utilized regardless of which direction the bandage is wrapped.

SUMMARY OF THE INVENTION

In accordance with this invention, there is provided an adjustable strip of elastic adapted to be wrapped around a portion of a patient's body to be bandaged in a plurality of overlapping convolutions so that the inner end thereof will be held in place by succeeding convolutions.

The bandage of this invention comprises a first fastener component of a flexible material of sufficient flexibility to conform to the curvature of the underlying convolutions of said strip when wrapped around said body portion and having an opening therein receiving a portion of said strip intermediate the ends of said strip. Said first fastener component is adjustable along the length of said strip so that it may be spaced from the outer end of the strip a distance substantially corresponding to the length of the outer convolution of the stretched strip. The first fastener component has an outer portion comprised of a front outer face and a rear outer face. Fibrous fastener fabric appears on at least a portion of a face selected from the group consisting of said front outer face and said rear outer face of said first fastener component.

The elastic bandage of this invention also is comprised of a second fastener component fixed to the outer end portion of said strip and adapted to cooperate with said outer portion said first fastener component to separably connect said components together so as to secure the outer end portion of said elastic strip with respect to the remainder of said strip when said bandage has been wrapped on a patient, said first fastener component being readily movable when said bandage is in an unwrapped, extended state, wherein complementary fibrous fabric material appears on at least a portion of a face selected from the front face and the rear face of said second fastener component.

DESCRIPTION OF THE DRAWINGS

The present invention will be more fully understood by reference to the following detailed description thereof, when read in conjunction with the attached drawings, wherein like reference numerals refer to like elements and wherein.

DESCRIPTION OF THE PREFERRED EMBODIMENTS

The elastic bandage of this invention is an elongated strip of fabric containing elastic threads or yarns or inelastic threads or yarns which have been so fabricated so as to create sufficient elasticity and acceptable stretch characteristics in the resulting fabric. Means for preparing such a strip or fabric, such as by knitting or weaving, are well known to those skilled in the art.

The strip of elastic bandage material is adapted to be wrapped around the portion of a patient's body to be bandaged in a plurality of overlapping convolutions so that the inner end thereof will be held in place by succeeding convolutions. The bandage is comprised of at least two separable fastener components. One of the fastener components is attached to the end of the bandage fabric strip, and the other is mounted upon the fabric strip intermediate the ends of the strip. Each of the fastener components is comprised of a fabric fastening material, such as VELCRO.

Processes for preparing VELCRO are well known to those skilled in the art. As is known to those skilled in the art, the VELCRO fastening system is comprised of at least one material containing fabric hooks comprised of synthetic resin and, on a mating surface, at least one material comprised of complementary fabric pile comprised of synthetic resin. One such process for making these type of material is described in U.S. Pat. No. 2,717,437 of de Mestral, which discloses a method for producing a velvet type fabric; the disclosure of U.S. Pat. No. 2,717,437 is hereby incorporated by reference into this specification. In this process, there is weaved together a plurality of weft threads and a plurality of warp threads of synthetic resin material (such as nylon), thereby forming loops with said auxiliary warp threads on one surface of the woven fabric. The loops so formed are submitted to a thermal source, thereby causing the loops to retain their shape and to form raised pile threads. The loops are then cut near their outer ends, thereby forming material-engaging means on at least a portion of said pile threads constituted by said cut loops.

Figure 2:
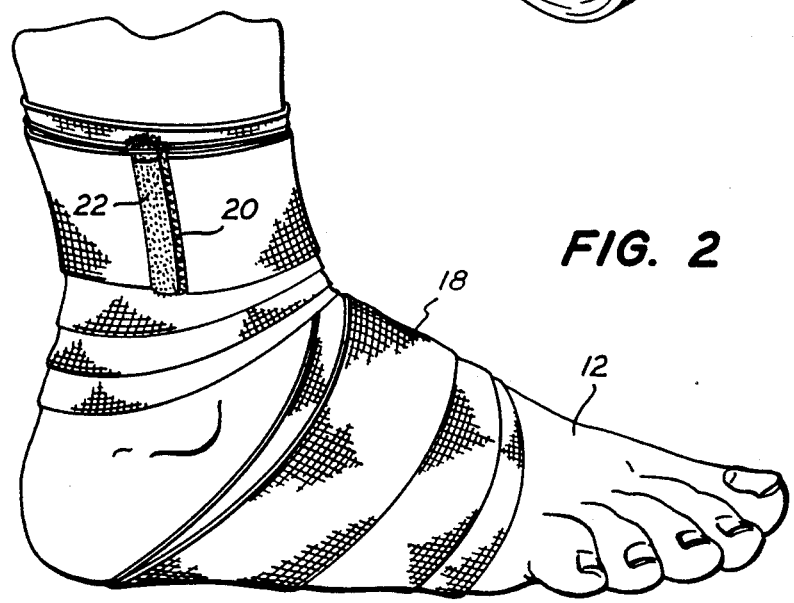
FIG. 2 is a perspective view of the bandage applied to a patient's foot and ankle.

Referring to FIG. 2 of the drawings, it can be seen that the bandage of this invention can be applied to a foot 12, a limb, or to the body of a patient, in much the same manner that prior art elastic bandages have been applied in the past. One end of an elongated strip of elastic fabric 14, which preferably is of knitted or woven construction, is brought into contact with the skin of the patient and the strip is wound around the foot 12 in a plurality of convolutions. Successive convolutions coincide or overlap in a manner such that all convolutions except the last one are held in place by friction. The last convolution is held in place by the fastener means of this invention which connects the outer end portion 16 of the fabric strip 14 to a fastener component 20.

The fastener means of this invention is a separable fastening and includes components which are mounted respectively adjustably on an intermediate portion 18 of the fabric strip 14 and fixedly on the outer end portion 16 of fabric strip 14. In the Figures, the fastener component which has been mounted upon the intermediate portion 18 of the fabric strip 14 is identified by numeral 20. It has a width slightly greater than the width of fabric strip 14 and is provided with an opening for receiving the intermediate portion 18 of the fabric strip 14. The fastener component which has been mounted upon the end portion 6 of fabric strip 14 is identified by numeral 22. One of fastener components 20 and 22 preferably has "VELCRO" (synthetic materials which adhere when pressed together) pile material on one or both of its surfaces, and the other of said components preferably has "VELCRO" (synthetic materials which adhere when pressed together) hook material on one or more of its surfaces. In the embodiment illustrated in FIG. 1, adjustable fastener component 20 has fabric hooks on its surfaces and fixed fastener component 22 has fabric pile material on its surfaces. In another embodiment, not shown, fastener component 20 has fabric pile material on its surface, and fixed fastener component 22 has fabric hook material on its surfaces. In one preferred embodiment, the fabric hook material is on the surface of the bandage which is opposite the body and is rotated as required, depending upon the direction of elastic bandage wrapping.

In yet another embodiment, not shown, each of fasteners 20 and 22 has fabric hook material on one of its surfaces and fabric pile material on the other of its surfaces so that, when the fasteners are pressed to each other, complementary mating surfaces are present.

Figure 1:
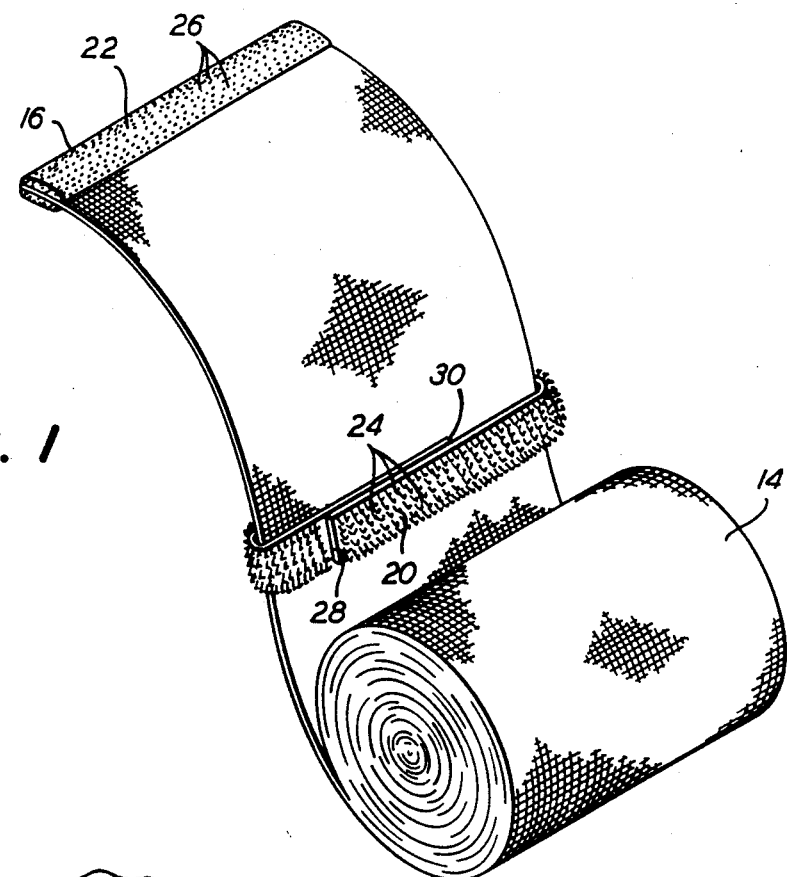
FIG. 1 is a perspective view of the adjustable bandage of this invention.

In the embodiment illustrated in FIG. 1, hooks 24 are present on adjustable fastener 20. When hooks 24 are pressed into the pile-like surface 26 of fixed fastener 22, they engage with the fabric of the latter. As is known to those skilled in the art, other types of fibrous fastening means can be used on fasteners 20 and 22.

In the embodiment illustrated in FIG. 1, adjustable fastener 20 is a band of fabric material with fibrous fastening material on at least one of its exterior surfaces. It is of a width slightly greater than the width of fabric strip to allow its movement along the length of fabric strip 14.

It is preferred that adjustable fastener 20 have fibrous fastening material on both of its front and rear exterior surface; this preferred embodiment is illustrated in FIGS. 1 and 2. With this preferred embodiment, because there is the fibrous fastening material on both of the surfaces, the adjustable fastener 20 can be utilized regardless of the direction the bandage is wrapped.

Adjustable fastener 20 may be constructed by means well known to those skilled in the art. Thus, e.g., one can cut a strip of fibrous fastener material, wrap it around fabric strip 14 so that it has a width slightly greater than the width of the fabric strip and is provided with an opening sufficient to receive the intermediate portion of the fabric strip, and then secure ends 28 and 30 of the fibrous fastener material strip together. Thus, e.g., one can cut a strip of fabric material, secure to part or all of the exterior surface of this fabric material the fibrous fastener material (such as, e.g., by sewing it on or gluing it on), and then use this fabric/fibrous fastener composite material for making the band 20 that encircles strip 14. Other means of constructing the adjustable fastener 20 will be apparent to those skilled in the art.

Adjustable fastener 20 may be constructed before it is used to encircle fabric strip 14; the strip 20 becomes an ellipse when it is in place on the fabric strip 14. In this embodiment, fastener 20 will have a diameter wide enough to accommodate elastic bandage 14 without crimping. This diameter will usually be from about 0.007 to about 2.0 inches, and it preferably will be from about 0.06 to about 0.25 inches.

It is preferred that the width of the fibrous fabric material on adjustable fastener 20 be from about 0.007 to about 3.0 inches and, preferably, from about 0.25 to about 1.0 inches. In the most preferred embodiment, the thickness of the fibrous fabric material is from about 0/007 to about 2.0 inches. As those skilled in the art are aware, the dimensions of the fibrous fastener may vary depending upon the size of the elastic bandage and the elastic tension of the material used in this manufacture, both of which can affect the strength of adherence.

Adjustable fastener 20 is usually positioned on the elastic bandage at a point less than one complete convolution from the end of the bandage when it is in its relaxed condition. Thus, in one embodiment, adjustable fastener 20 is usually located form about 2 to about 8 inches from the end 16 of the bandage.

Fixed fastener 22 also has fibrous fastener material on at least one of its front or back surfaces, although it is preferred to use said fibrous fastener material on both of said surfaces. The fibrous fastener material used on fixed fastener 22 is complementary to that used on adjustable fastener 20. The term complementary, as used in this specification, refers to a fibrous fastener material which will adhere to the fibrous fastener material on the other fastener. Either the front surface and/or the back surface of adjustable fastener 22 must contain a fibrous fastener material which is complementary to the fibrous fastener material which appears on the front surface and/or the back surface of fixed fastener 22. Thus, e.g., if VELCRO hook material is used on the front surface of adjustable fastener 20, complementary VELCRO pile material should be used on the front surface of fixed fastener 22. Thus, e.g., if the hook material is used on the rear surface of fixed fastener 22, then the complementary pile material should be used on the rear surface of adjustable fastener 20. In one preferred embodiment, VELCRO pile material appears on both the front and the back of fixed fastener 22.

Fixed fastener 22 can be constructed by conventional means well known to those skilled in the art. Thus, by way of illustration, a band of fibrous fabric material which is complementary to the fibrous fabric material used on adjustable fastener 22 can be attached to the front and/or the back surface of strip 14 at or near its end 16. In one embodiment, the strip of complementary fibrous fastener material is folded over the end 16 of strip 14 and attached thereto by glue and/or sewing.

Each of adjustable fastener 20 and fixed fastener 22 are flexible and deformable so that they can conform somewhat to the curvature of the limb to which the bandage is applied.

It is to be understood that the aforementioned description is illustrative only and that changes can be made in the article of manufacture, the elements and their proportions, and in the sequence of combinations and process steps as well as in other aspects of the invention discussed herein without departing from the scope of the invention as defined in the following claims.

I claim:
1. An adjustable strip of elastic adapted to be wrapped around a portion of a patient's body to be bandaged in a plurality of overlapping convolutions so that the inner end thereof will be held in place by succeeding convolutions, comprising:
    (a) a first fastener component of a flexible material of sufficient flexibility to conform to the curvature of the underlying convolutions of said strip when wrapped around said body portion and having an opening therein receving a portion of said strip intermediate the ends of said strip, wherein:
        1. said first fastener component is adjustable along the length of said strip so that it may be spaced from the outer end of the strip a distance substantially corresponding to the length of the outer convolution of the stretched strip,
        2. said first fastener component has an outer portion comprised of a front outer face and a rear outer face, and
        3. fibrous fastener fabric appears on both of said front outer face and said rear outer face of said first fastener component;
    (b) a second fastener component fixed to the outer end portion of said strip and being adapted to cooperate with said outer portion of said first fastener component to separably connect said components together so as to secure the outer end portion of said elastic strip with respect to the remainder of said strip when said elastic strip has been wrapped on a patient, said first fastener component being readily movable when said elastic strip is in an unwrapped, extended state, wherein complementary fibrous fabric material appears on both of the front face and the rear face of said second fastener component.

2. The adjustable strip as recited in claim 1, wherein said fibrous fastener material appears on the front face of said first fastener component.

3. The adjustable strip as recited in claim 2, wherein said fibrous fastener material appears on the rear face of said first fastener component.

4. The adjustable strip as recited in claim 3, wherein said fibrous fastener material appears on substantially the entire portion of the front face of said first fastener component.

5. The adjustable strip as recited in claim 4, wherein said fibrous fastener material appears on substantially the entire portion of the rear face of said first fastener component.

6. The adjustable strip as recited in claim 5, wherein the same fibrous fastener material appears on both the front and rear face of said first fastener component.

7. The adjustable strip as recited in claim 6, wherein said fibrous fastener material consists essentially of nylon.

8. The adjustable strip as recited in claim 7, wherein complementary fibrous fastener material appears on both the front face and the rear face of said second fastener component.

9. The adjustable strip as recited in claim 8, wherein complementary fibrous fastener material appears across the entire surface of both the front face and the rear face of said second fastener component.

10. The adjustable strip as recited in claim 9, wherein said complementary fibrous fastener material consists essentially of nylon.

* * * * *